US006428816B1

(12) United States Patent
Schlipalius et al.

(10) Patent No.: US 6,428,816 B1
(45) Date of Patent: Aug. 6, 2002

(54) CAROTENOID AGENT FOR INHIBITING THE CONVERSION OF EPITHELIAL CELLS TO TUMORS

(75) Inventors: Lance Elliot Schlipalius, Ashwood (AU); Julie A. Buckmeier, Long Beach; Frank L. Meyskens, Jr., Irvine, both of CA (US)

(73) Assignee: Cognis Australia Pty., Ltd., Broadmeadows (AU)

( * ) Notice: Subject to any disclaimer, the term of this patent is extended or adjusted under 35 U.S.C. 154(b) by 0 days.

(21) Appl. No.: 08/718,522

(22) PCT Filed: Apr. 10, 1995

(86) PCT No.: PCT/AU95/00199

§ 371 (c)(1),
(2), (4) Date: Jan. 16, 1997

(87) PCT Pub. No.: WO95/27483

PCT Pub. Date: Oct. 19, 1995

Related U.S. Application Data

(63) Continuation-in-part of application No. 08/743,174, filed on Nov. 5, 1996, now Pat. No. 6,132,790, which is a continuation of application No. 08/604,359, filed on Feb. 21, 1996, now abandoned, which is a continuation of application No. 08/204,188, filed as application No. PCT/AU92/00470 on Sep. 7, 1992, now abandoned.

(30) Foreign Application Priority Data

Oct. 8, 1994 (AU) .............................. PM4931

(51) Int. Cl.[7] .......................... A61K 35/78; A61K 31/07
(52) U.S. Cl. ...................... 424/725; 424/773; 514/725; 514/938
(58) Field of Search ............................. 424/195.1, 725; 424/773; 514/725, 938

(56) References Cited

U.S. PATENT DOCUMENTS 5,230,836 A  *  7/1993  Todd, Jr. .................... 252/407
5,705,180 A  *  1/1998  Schlipalius ................. 424/423
6,132,790 A  * 10/2000  Schilpalius ................. 426/540

FOREIGN PATENT DOCUMENTS

WO    93/04598   *  3/1993
WO    94/21231   *  9/1994

OTHER PUBLICATIONS

Mathews–Roth, Oncology, 39:33–37, 1982.*
Mathews–Roth, Photochem. and Photobiol., 37, 509–511, 1983.*
Mathews–Roth, Fed. Proc., 46:1890–1893, 1987.*
Ghosh et al., Molecular and Cellular Biology, 13:6992–6999, 1993.*
Georgiadis et al., J. Investigative Dermatology, 98:657, Abstract #631, 1992.*
Rousseau et al., Free Radical Biology and Medicine, 13:407–433, 1992.*
Bain et al., Ann. Epidemiol., 3:235–238, 1993.*
Epstein, Photochem. Photobiol., 25:211–213, 1977.*
van Poppel, Eur. J. Cancer, 29A:1335–1344, 1993.*
"Polysorbates", 7742, Editor Susan budavari et al., *The Merck Index An Encyclopedia of Chemicals, Drugs, and Biologicals*, 1996, 12th Edition, Merck Research Laboratories Division of Merck & Co., Inc. Whitehouse Station, NJ.
Moon RC, "Comparative Aspects of Carotenoids and Retinoids as Chemopreventive Agents for Cancer," *J. Nutr.* (1989) 119:127–134.
Bertram, JS Pung A., Churley M. et al., "Diverse Carotenoids Protect Against Chemically Induced Neoplastic Transformation," *Carcinogenesis* (1991) 12:671–678.
Hazuka MB, Prasad–Edwards J., Newman F., et al., "Beta–carotene Induces Morphological Differentiation and Decreases Adenylate Cyclase Activity in Melanocyte Cells in Culture," *J. Am. Coll. Nutr.* (1990) 9:143–149.
Schultz TD, Chew BP, Seatman WR et al, "Inhibitory Effect of Conjugated Dienoic Derivatives of Linoleic Acid and Beta–carotene on the in vitro Growth of Human Cancer Cells," *Canc Letters* (1992) 63:125–133.
Schwartz JL, Shklar G, "The Selective Cytotoxic Effect of Carotenoids and a–tocopherol on Human Cancer Cell Lines in vitro," *J. Oral Maxillofac Surg* 0:367–373.
Schwartz JL, Tanaka J., Khandekar V, et al, "Beta–Carotene and/or Vitamin E as modulators of Alkylating Agents in SCC–25 Human Squamous Carcinoma Cells," *Canc Chemother–Pharmacol* (1992) 29:207–213.
Zhang L–X, Cooney RV, Bertram JS, "Carotenoids Enhance Gap Junctional Communication and Inhibit Lipid Peroxidation in C3H/10T1/2 Cells; Relationship to Their Cancer Chemopreventive Action," *Carcinogenesis* (1991) 12:2109–2114.
Zhang L–X, Cooney RV, Bertram JS, "Carotenoids Up–regulate Connexin 43 Gene Expression Independent of Their Provitamin A or Antioxidant Properties," *Canc Res* (1992) 52:5707–5712.
Gilchrest BA, Soler NA, Staff JS and Mihm MC Jr., "The Human Sunburn Reaction: Histologic and Biochemical Studies," *J. Am. Acad. Dermatol.* (1981) 5:411–422.
Simon, MM et al, "UVB Light Induces Nuclear Factor Kappa B (NF Kappa B) Activity Independently From Chromosomal DNA Damage in Cell–Free Cytosolic Extracts," *The Journal of Investigative Dermatology*, 102 (1994) 3:422.

* cited by examiner

Primary Examiner—Christopher R. Tate
(74) *Attorney, Agent, or Firm*—John E. Drach; Aaron R. Ettelman

(57) ABSTRACT

A method of inhibiting carcinogen mediated conversion of melanocyte cells and protecting DNA against carcinogen-mediated damage by administering a composition comprising a water insoluble carotenoid such as beta-carotene is disclosed.

19 Claims, 10 Drawing Sheets

CAROTENOID AGENT FOR INHIBITING THE CONVERSION OF EPITHELIAL CELLS TO TUMORS

Figure 1:
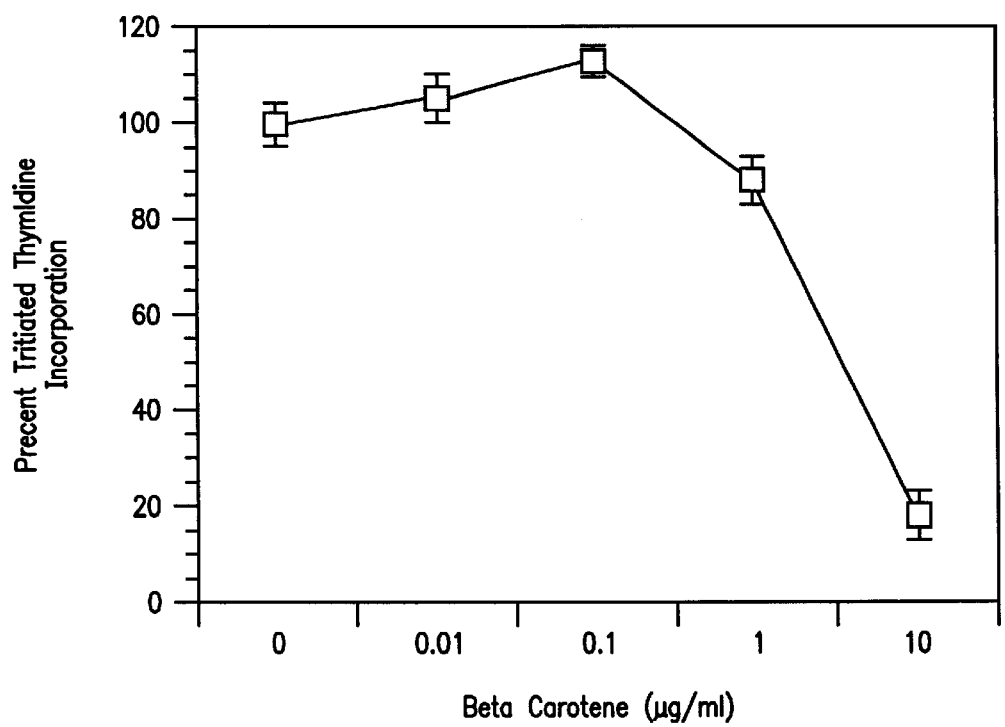

This application is a continuation-in part of U.S. application Ser. No. 08/743,174, filed Nov. 5, 1996, now U.S. Pat. No. 6,132,790, which is a continuation of U.S. application Ser. No. 08/604,359, filed Feb. 21, 1996, now abandoned, which is a continuation of U.S. application Ser. No. 08/204, 188, filed on Apr. 29, 1994, now abandoned, which is a 371 of PCT/AU92/00470 filed on Sep. 7, 1992. Benefit of these applications is claimed pursuant to 35 U.S.C. §120.

FIELD OF THE INVENTION

The invention relates to a cartenoid agent for inhibiting the conversion of epithelial cells to tumors and a method for such treatment. More particularly, the invention relates to a cartenoid agent for inhibiting the conversion of melanocytes to melanomas and a method foe such treatment.

BACKGROUND TO THE INVENTION

Although the description which follows is specifically directed to melanocytes and melanomas, it will be clear to a person skilled in the art that similar comments apply with respect to other types of epithelial cells.

Melanomas originate from a change in normal skin cells, melanocytes, which produce the brown pigment melanin we recognise as tan. Moles freckles result from areas of the skin with many melanocytes.

Melanomas are caused generally by the exposure of skin to sunlight. Persons of fair complexion have the greatest risk especially those who develop moles.

The influence of light on melanocytes is one way by which they can be changed to grow and divide differently, possibly causing a melanoma. The melanomas may be malignant, spreading to other parts of the body. Melanomas which do not spread are called benign melanomas.

Although melanomas normally form on exposed skin they can start in places such as the mouth.

Melanomas grow in size and need to be surgically removed before they spread and invade other parts of the body. If the melanomas spread to the inner organs, removal and treatment is more difficult and chemotherapy or radiotherapy need to be employed. For this reason, if melanocytes can be inhibited from converting to melanomas, the associated problems with the treatment of melanomas can be similarly reduced.

It has been hypothesized that carotenoids and in particular beta-carotene may reduce the risk of breast, lung, colon, prostate and cervical cancer, heart disease and stroke and may retard macular degeneration. In this respect, one hypothesis is that in mammals beta-carotene is converted to vitamin A and vitamin A analogues or retinoids (see Moon RC: Comparative aspects of carotenoids and retinoids as chemopreventive agents for cancer. J Nutr 119:127–134, 1989). It is this pro-vitamin A activity and the ability to prevent oxidative damage that has made carotenoids and, in particular, beta-carotene a compound of interest in chemopreventive studies. For instance, anti-oxidants are used, amongst other things, to quench free radicals that are by-products of normal metabolism in cells.

Beta-carotene has also been used in the treatment of erythropoietic protoporphyria (EPP). EPP is a genetic disease causing an inadequacy in the metabolism of porphyrin compounds. It results in a rapid blistering of the skin on exposure to sunlight.

Although, the effectiveness of carotenoids has been hypothesized in reducing the risk of certain instances of cancer, no studies have demonstrated the possible inhibiting effect of carotenoids in the conversion of melanocytes to melanomas.

For this reason, investigations were undertaken to determine the efficacy of carotenoids in inhibiting or reducing the conversion of melanocytes to melanomas. As part of this investigation, it was necessary to consider the difficulties in the use of carotenoids in human applications because of the nature and chemical properties of carotenoids.

Carotenoids are lipophyllic and therefore not soluble in water in useful quantities. It is believed that they are transported in the bloodstream in conjunction with low density lipoproteins.

To date several in vitro studies have taken place to determine th effect of beta-carotene on normal and transformed cell types using solvents to solubilize the beta-carotene such as tetrahydrofuran, butanol, chloroform, hexane, dimethylsulfoxide, ethanol or in a liposome micelle. Previous liposome preparations have shown toxicity in cell line cultures as well as being limited in application (see Betram J S, Pung A, Churley M, et al: Divers carotenoids protect against chemically induced neoplastic transformation. Carcinogenesis 12:671–678, 1991; Hazuka M B, Prasad-Edwards J, Newman F, it al; Beta-carotene induces morphological differentiation and decreases adenylated cyclase activity in melanocyte cells in culture. J Am Coll Nutr 9:143–149, 1990; Schultz T D, Chew B P, Seatnan W R, et al: Inhibitory effect of conjugated dienoic derivatives of linolcic acid and beta-carotene on the in vitro growth of human cancer cells. Canc Letters 63:125–133, 1992; Schwartz J L, Shaklar G: The selective cytotoxic effect of carotenoids and a-tocopherol on human cancer cell lines In vitro. J Oral Maxillofac Surg 50:367–373, 1992; Schwartz J L, Tanaka J, Khandekar V, et al: Beta-Carotene and/or Vitamin E as modulators of alkylating agents in SCC-25 human aquamous carcinoma cells. Canc Chemother Pharmacol 29:207–213, 1992; Zhang L-X, Cooney R V, Bertram J S; Carotenoids enhance gap juctional communication and inhibit lipid peroxidation in C3H/10T1/2 cells; relationship to their cancer chemopreventive action. Carcinogenesis 12:2109–2114, 1991; and Zang L-X, Cooney R V, Bertram J S ; Carotenoids Up-regulate connexin 43 gene expression independent of their provitamin A or antioxidant properties. Canc Res 52:5707–5712, 1992). These solvents have been found to have a toxic effect which is dose dependent. These solvents are also incompatible with human blood or lymph for the purposes of intravenous or injectable preparations.

Thus, in administering carotenoids, care must be taken to use appropriate carriers. Accordingly we carried out in vitro studies to determine the efficacy of carotenoids in inhibiting the conversion of epithelial cells to tumors and more particularly, the conversion of melanocytes to melanomas.

SUMMARY OF THE INVENTION

According to the present invention, a carotenoid agent is provided for inhibiting the conversion of epithelial cells to tumors, the agent including an effective amount of a water insoluble carotenoid component in a suitable non-toxic carrier medium.

The invention also provides a method of inhibiting the conversion of epithelial cells to tumors, including the step of applying to the cells, an effective amount of a water insoluble carotenoid component in a suitable non-toxic carrier medium.

The invention further provides a method of treating epithelial cells, so as to inhibit their conversion into tumors, including the step of applying to the cells, an effective amount of a water insoluble carotenoid component in a suitable non-toxic carrier medium.

The epithelial cell may be of mammalian origin. Preferably, the cell is a skin cell. It is particularly preferred that the skin cell is a melanocyte. In an even more preferred form of the invention, the epithelial cell is a human cell, and in a particularly preferred form of the invention, a human melanocyte.

Preferably, the water insoluble carotenoid component includes beta-carotene. In a yet further preferred form of the invention, the water insoluble carotenoid component includes from 2% to 50% by weight of beta-carotene. It is further preferred that the water insoluble carotenoid component includes from 20% to 40% by weight of bets-carotene. Even more preferably, the water insoluble carotenoid component includes 30% by weight of beta-carotene.

Preferably, the carrier medium includes a suspending agent selected from the group comprising fatty acids, triglycerides lipids, non-saponifiable lipid preparations, soluble hydrocarbons and combinations thereof.

Preferably, the triglycerides lipids are selected from the group comprising fats and/or oils derived from plant sources. The fats and/or oils may be derived from plant sources (in which case, it is particularly preferred that seed oils, such as cotton seed oil, sunflower oil or combinations thereof are used), or from animal sources (such as meat and fish). Seed oils are particularly preferred, and soya bean oil is an especially preferred oil for use in the carrier medium.

Preferably further, the water insoluble carotenoid component constitutes from 0.1% to 10% by weight of the agent. It is particularly preferred that the water insoluble carotenoid component constitutes from 1% to 5% by weight of the agent.

The non-toxic carrier medium preferably also includes an emulsifier. Preferably, the emulsifier is selected from the group including TWEEN® (polysorbate), glycerol fatty acid esters and acetylated esters of fatty acids. Glycerol mono-oleate is a particularly preferred emulsifier.

Preferably, the non-toxic carrier medium also includes a water soluble dispersing agent. It is particularly preferred that the water soluble dispersing agent is a sugar or a polyol. It is especially preferred that the water soluble dispersing agent is selected from the group including sorbitol and glycerol.

In all forms of the invention, preferably, the effective amount of the carotenoid agent contacting the melanocyte cells is from 0.1 to 10.0 micrograms/ml and more preferably, 0.3 to 3.0 micrograms/ml. These concentrations are achieved by dilution with suitable diluents. More preferably the diluting solution is selected from media suitable for the growth of the cells, aqueous buffers, normal intravenous preparations (including isotonic saline or 5% dextrose solution) and blood serum and combinations of the foregoing.

The term "mixture" as used herein is intended to include various physical forms including emulsions, solutions and crystal suspensions.

EXAMPLES

The following examples demonstrate the effectiveness of carotenoid compositions in the treatment of melanocytes and the relative non-toxicity of those compositions.

The examples that follow will now be described with reference to the accompanying drawings, in which:

BRIEF DESCRIPTIONS OF THE DRAWINGS

FIG. 1 is a graph showing the effect of beta-carotene on DNA synthesis in normal human melanocytes. In summary, while DNA synthesis was largely inhibited at the highest beta-carotene dose, the lower doses had little or no effect. The 10 $\mu$g/ml dose was chosen as the pre-treatment dose for the UV experiments as it offered the highest beta-carotene concentration achievable with minimal effect on DNA synthesis. Beta-carotene was incubated with the melanocytes for 24 hours. Each data point is the mean of 6 wells+/−% std. error as compared to control.

Figure 2:
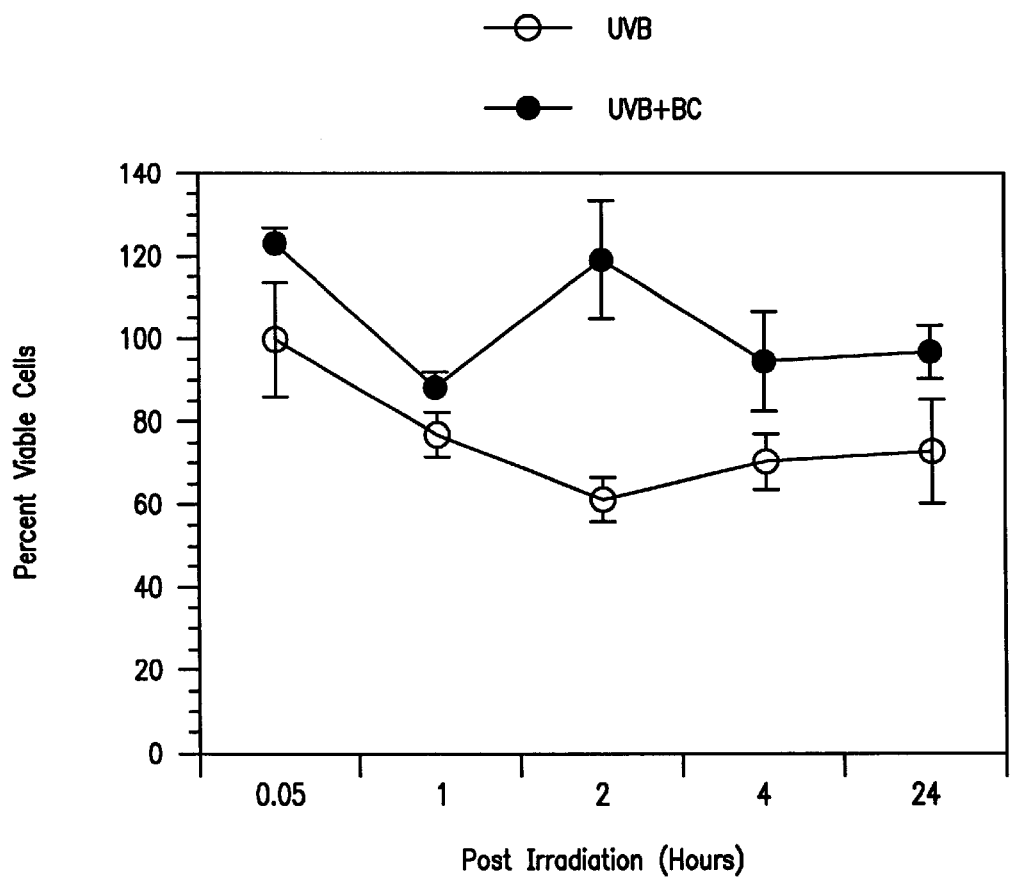
Figure 3A:
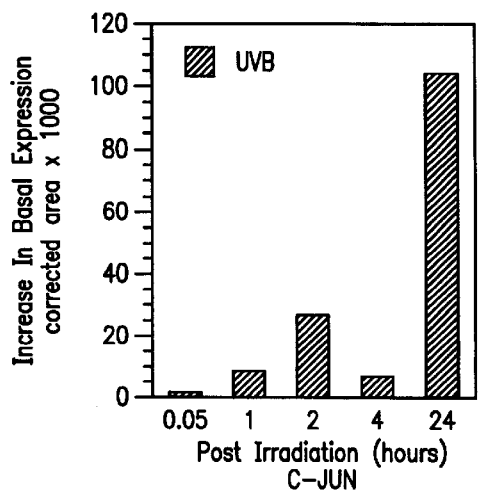
Figure 3B:
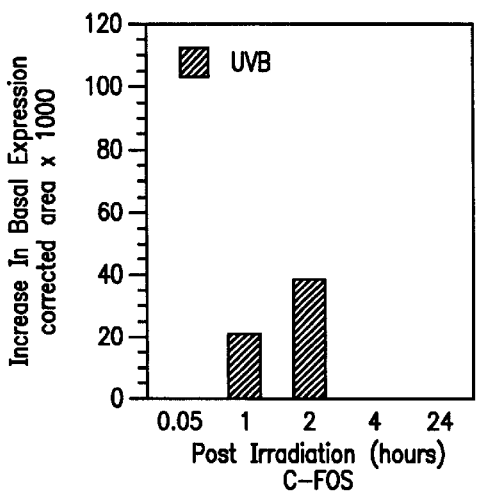
Figure 3C:
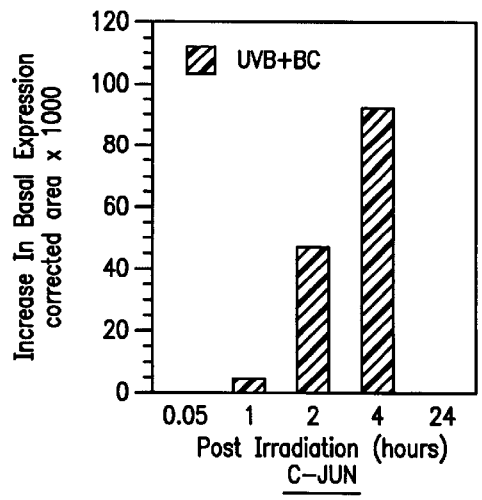
Figure 3D:
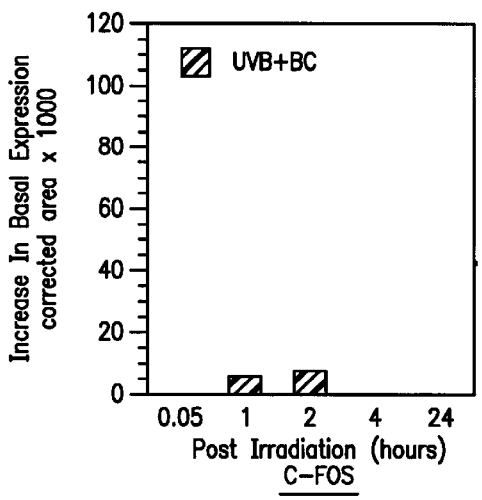
Figure 3E:
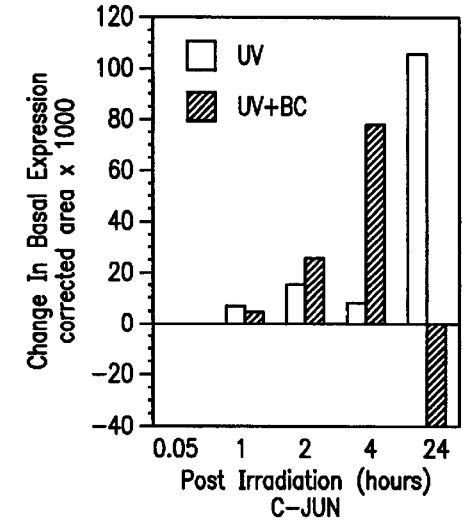
Figure 3F:
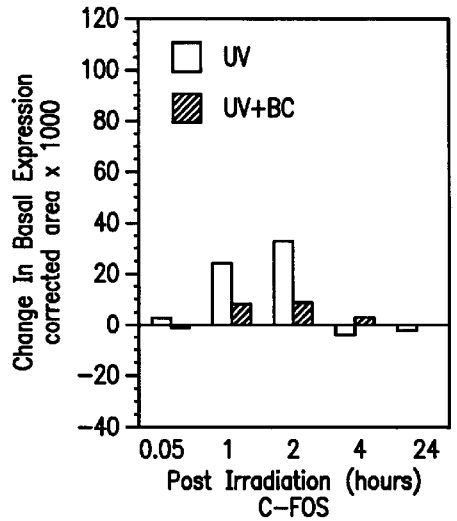

FIG. 2 is a graph showing the viability of normal human melanocytes following UV-B irradiation with and without beta-carotene. In summary, immediately following 500 mJ/cm$^2$ of UV-B (0.05) hr, cell viability increased almost 20% with beta-carotene present as compared to UV-B alone. This effect remained for the duration of the time course. Each data point is the mean of 3 wells +/−% std. error as compared to controls.

FIG. 3 are graphs showing the northern analysis of melanocytes exposed to UV-B irradiation with and without beta-carotene. In summary, the largest induction of c-jun by UV-B occurred 24 hours following a 500 mJ/cm$^2$ exposure (36.2 fold over basal level), Maximal induction of c-fos occurred 2 hours following irradiation with expression level 57 fold above basal. The induction of c-fos by UV-B was essentially blocked by beta-carotene. C-jun expression was increased 11.1 fold by beta-carotene four hours following irradiation while at 24 hours, the induction by UV-B was completely blocked. Basal expression level of these genes without beta-carotene or UV-B has been subtracted from all RNA levels shown. Blots were corrected for loading by 18S.

Figure 4:
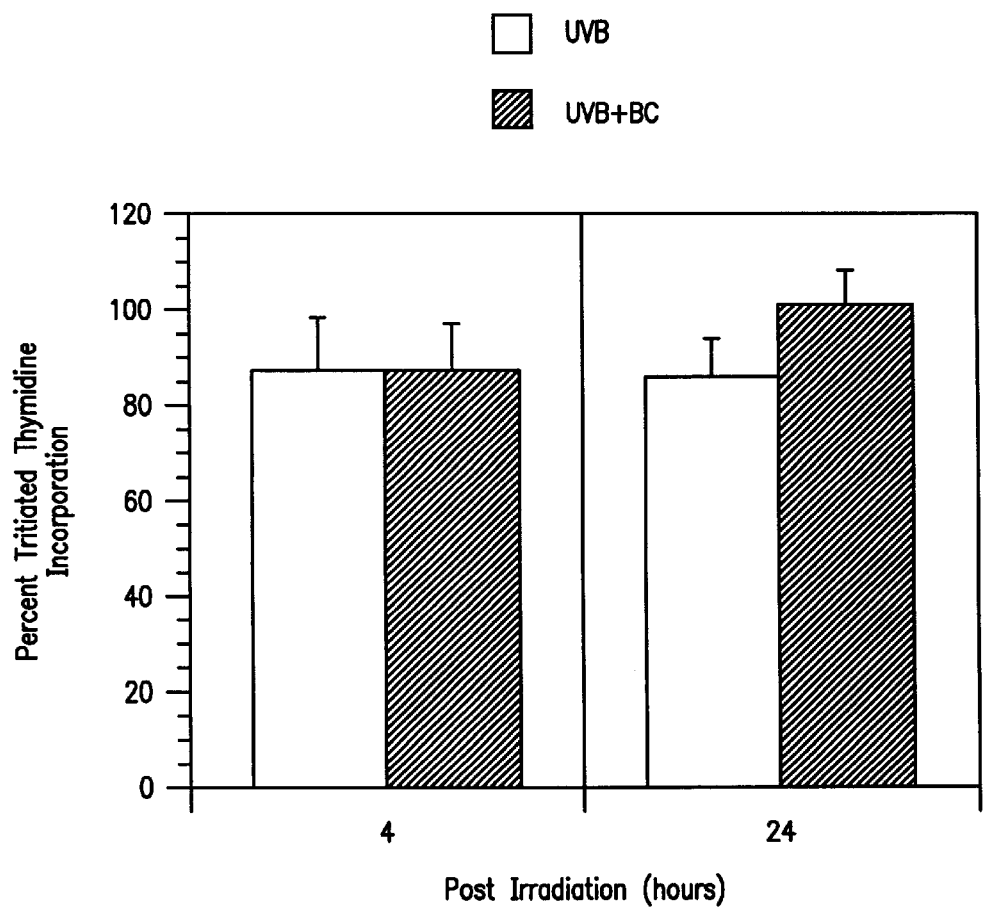

FIG. 4 is a graph showing DNA synthesis in normal human melanocyte with and without beta-carotene. In summary, beta-carotene pre-treatment increased DNA synthesis 24 hours following 400 mJ/cm$^2$ of UV-B. This effect was not seen 4 hours after irradiation. Each data point is the mean of 6 wells +/−% std. error as compared to controls.

Figure 5:
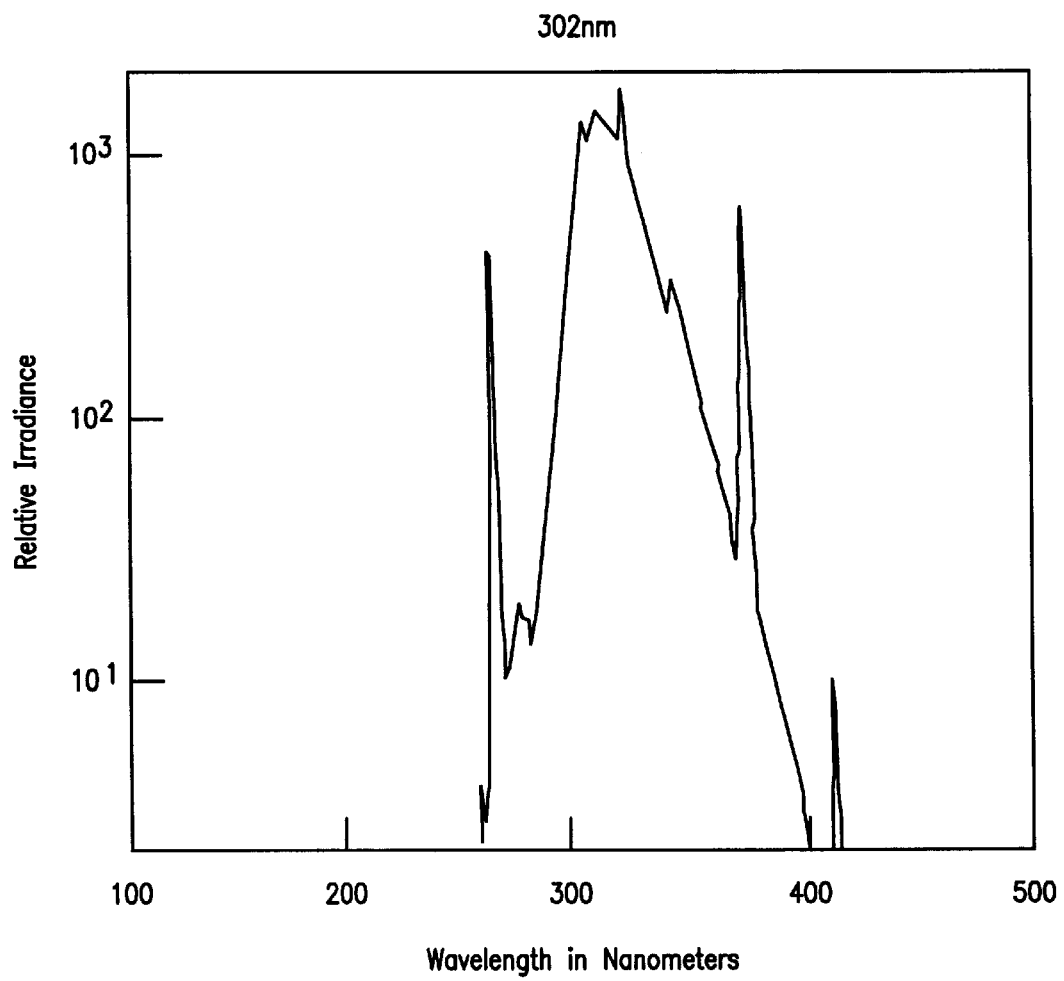
Figure 6A:
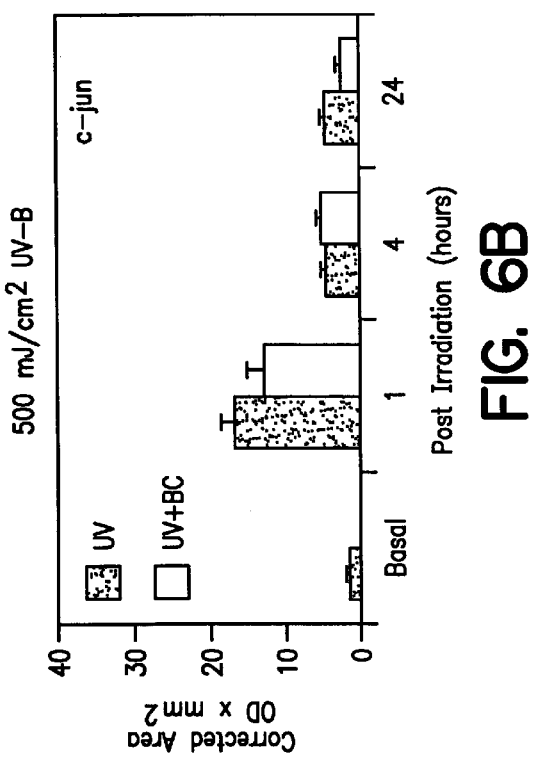
Figure 6B:
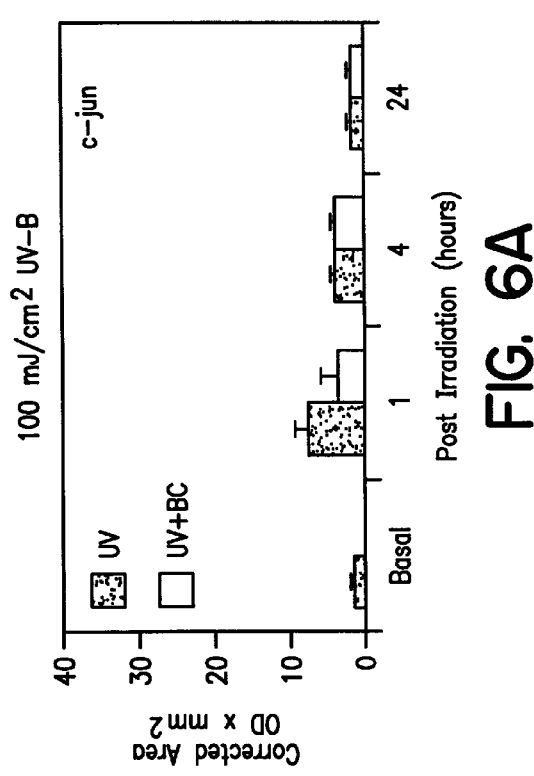
Figure 6C:
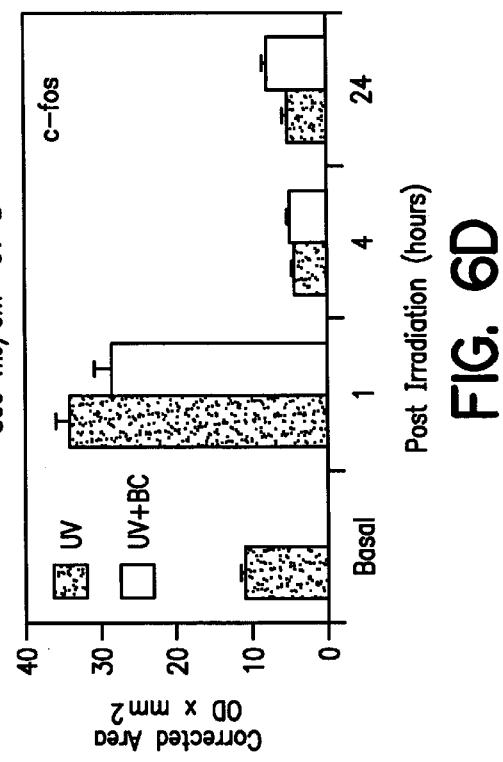
Figure 6D:

FIG. 5 is a graph showing the spectrum distribution for the UVP bulbs used in the Stratalinker Crosslinker apparatus which was used in the experiments.

FIG. 6 shows four histograms depicting the results of experiments comparing the effects of beta-carotene treatment on melanocytes exposed to UV-B irradiation. In summary, melanocytes were treated for 24 hours with or without beta-carotene (1 ug/ml) with the appropriate controls. Media was then removed and cells were exposed to 100 or 500 mJ/cm$^2$ of UV-B. Fresh media was then added and cells were incubated for an additional 1, 4 and 24 hours and total RNA isolate. This histogram is representative of four independent Northerns (corrected for loading) from four normal Caucasian melanocyte lines.

Figure 7:
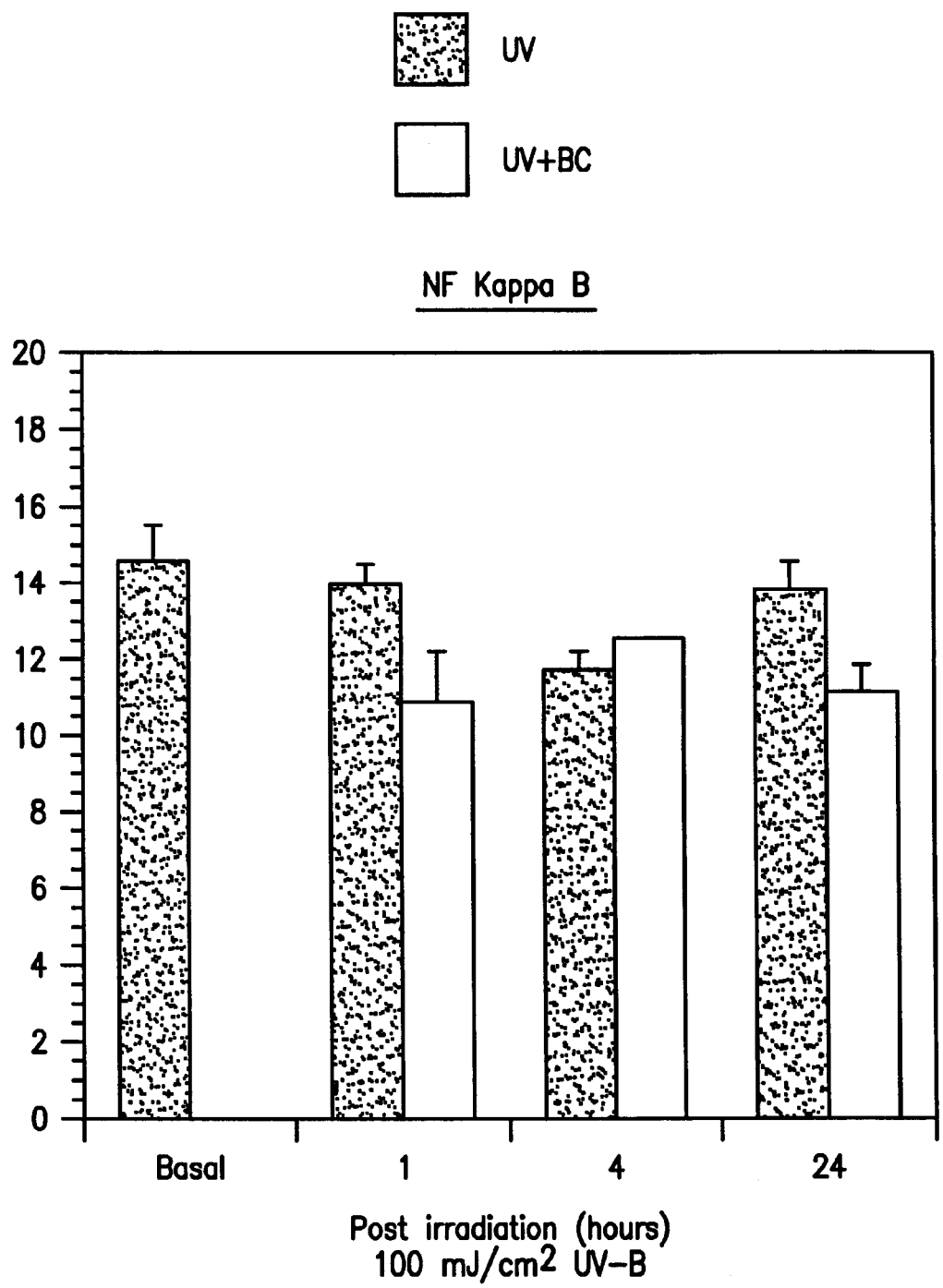

FIG. 7 shows the results of beta-carotene treatment on the DNA binding activity of cells exposed to 100 mJ/cm$^2$ UV-B irradiation.

Figure 8:
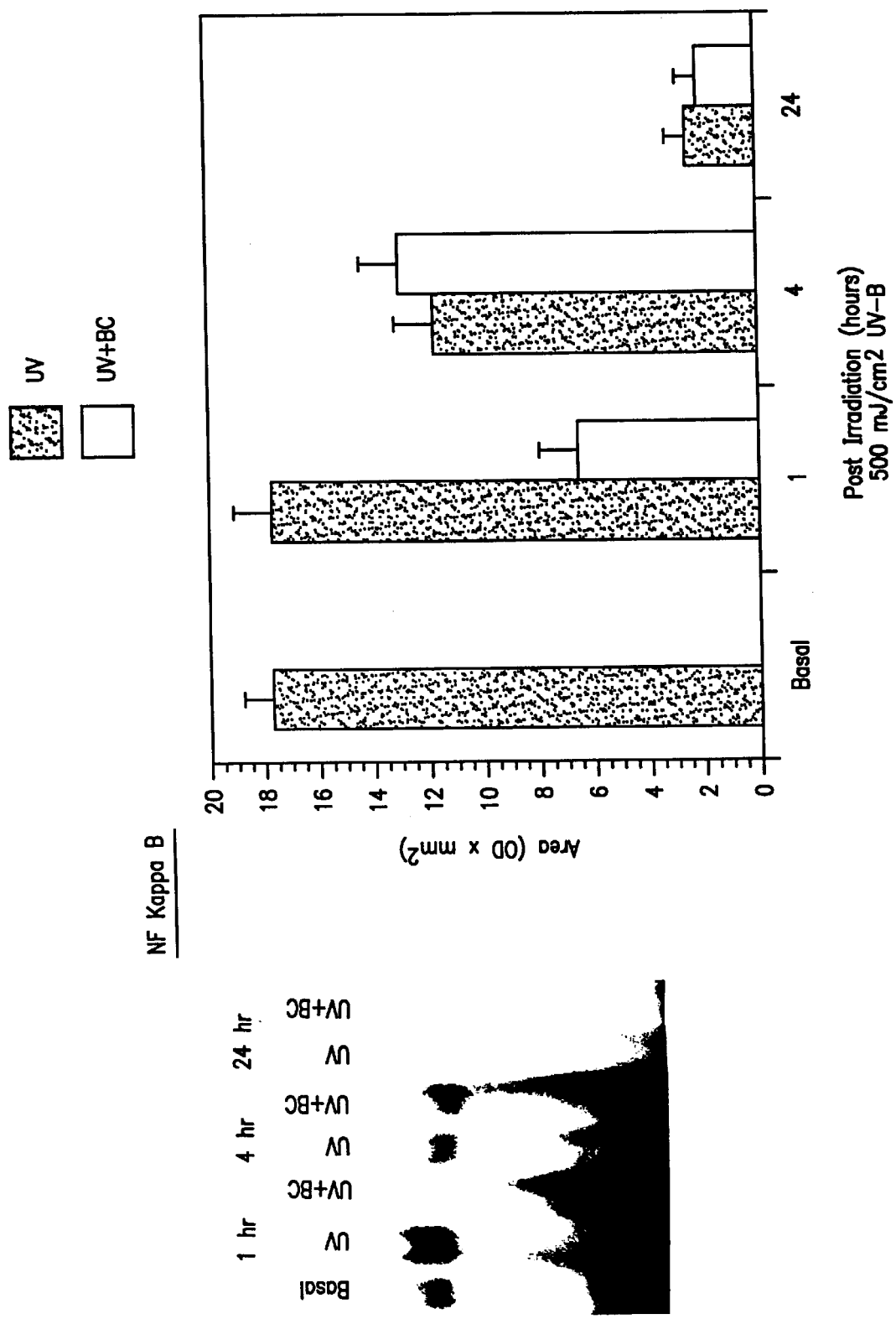

FIG. 8 shows the results of beta-carotene treatment on the DNA binding activity of cells exposed to 500 mJ/cm$^2$ UV-B irradiation. In summary, gel mobility shift assay using a NF Kappa B consensus sequence was performed to determine DNA binding activity of nuclear extracts from four normal Caucasian melanocyte (NCM) lines. NCM were pre-treated with 1.0 ug/ml of beta-carotene for 24 hours followed by 500 mJ/cm$^2$ of UV-B and assayed at 1.4 and 24 hours following irradiation.

Figure 9:
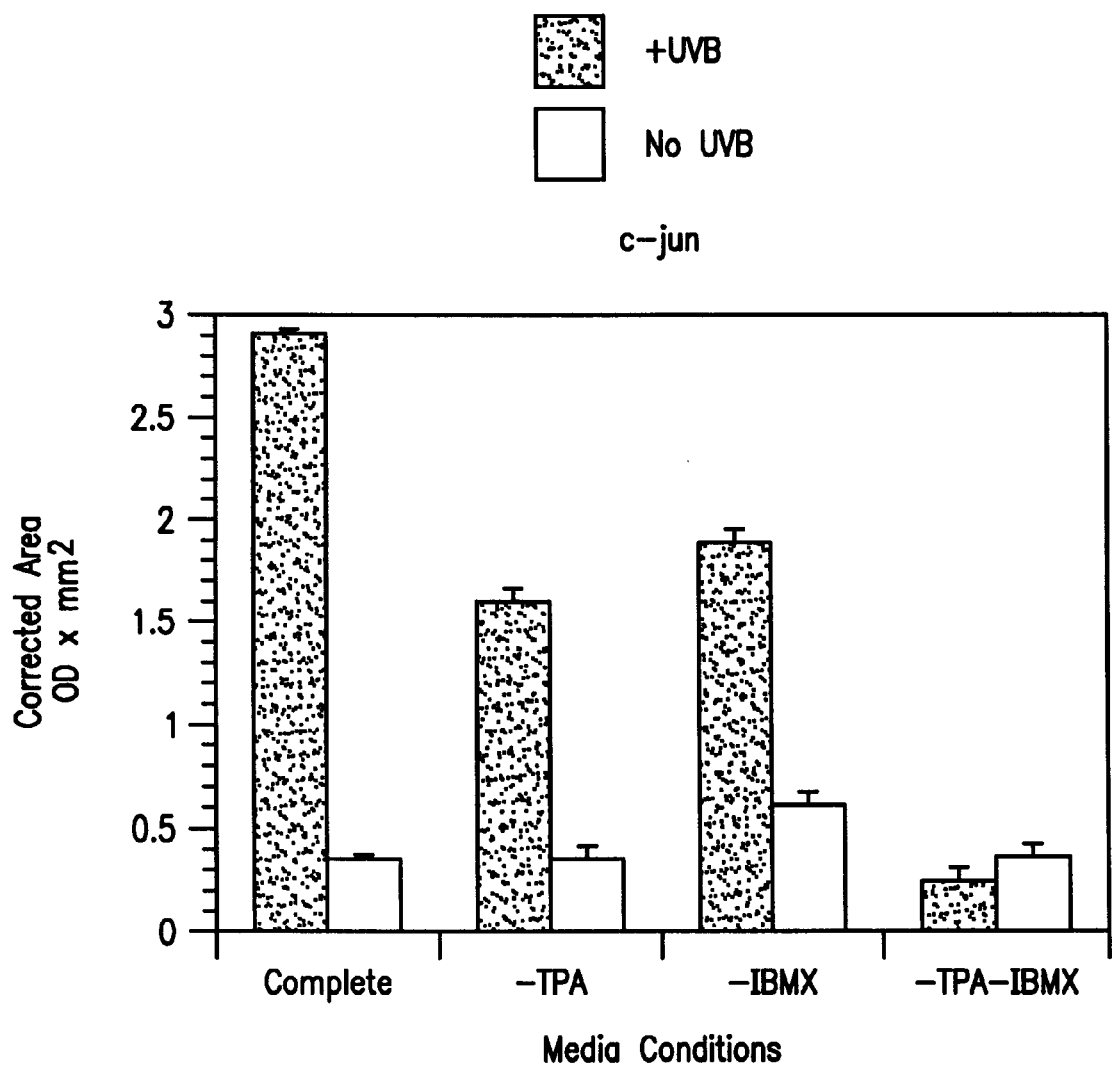

FIG. 9 shows the effects of treating human melanocytes exposed to O-Tetradecanoylphorbol 13-acetate (TPA), 3-Isobutyl 1-Methyl Xanthine (IBMX) and a combination of TPA and IBMX on the total RNA synthesis of those melanocytes subsequently irradiated with UVB. In summary, melanocytes were treated for 24 hours with or without TPA (10 ng/ml) or IBMX (0.1 mM) with the appropriate controls. Media was then removed and cells exposed to UV-B received a dose of 100 mJ/cm$^2$. Fresh media was then added with or without TPA or IBMX and cells were incubated for 1 hour following irradiation and total RNA was isolated. This histogram is representative of two independent Northerns (corrected for loading) from two normal neonatal Caucasian melanocyte lines.

Figure 10:
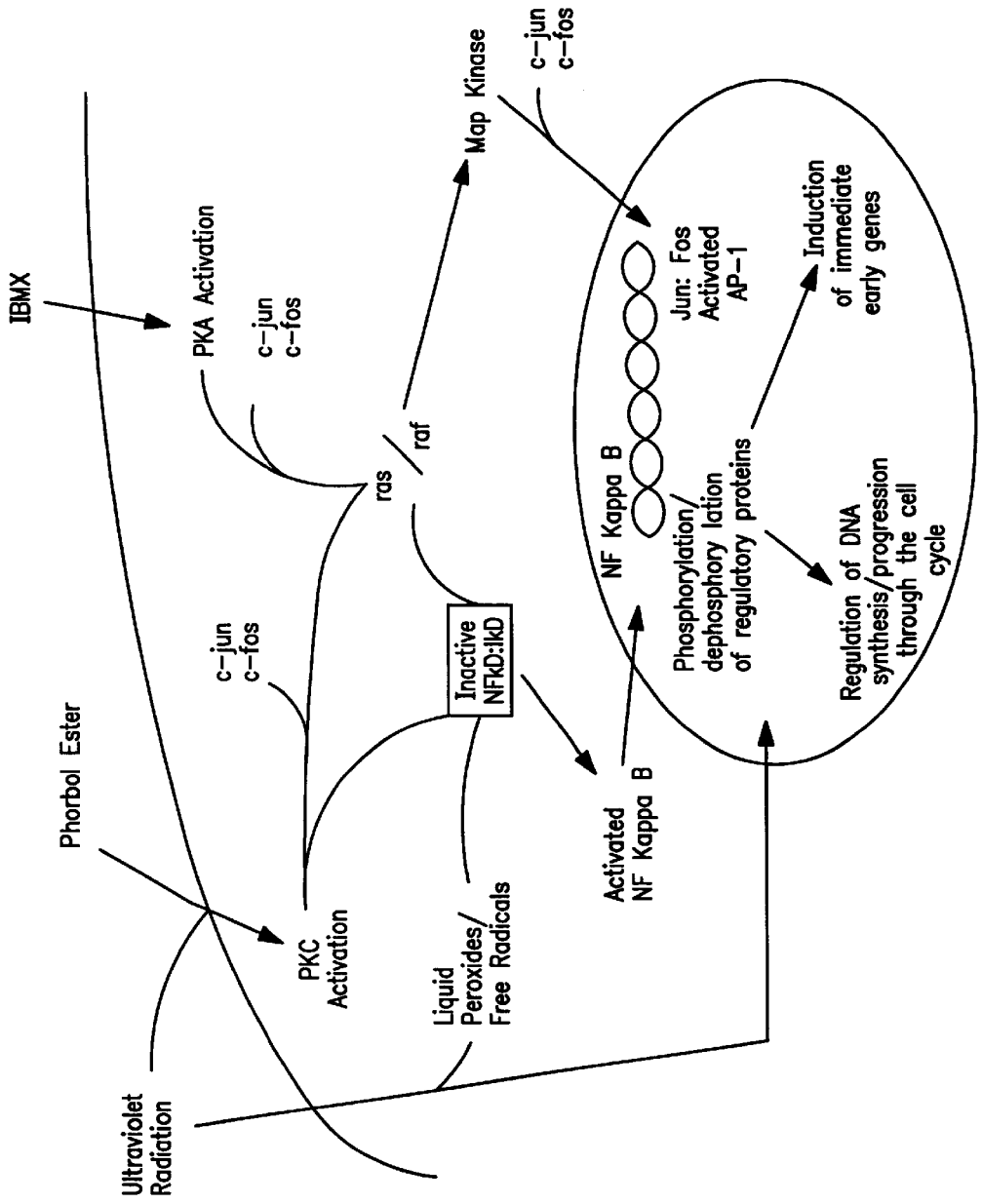

FIG. 10 shows an overview of the intracellular mechanisms putatively responsible for the reaction of human melanocytes to ultra-violet radiation exposure.

FIGS. 1 and 5 refer to "Percent Tritiated Thymidine Incorporation" which is a measure of DNA synthesis activity.

Details of the experiments conducted in relation to the invention are as follows.

Materials (a) Cell Cultures

Human neonatal foreskins were placed in 0.25% trypsin at 4° C. overnight. Following this incubation, the tissue was scraped to recover the melanocytes. The melanocytes were cultured in MCDB 151 (Sigma) medium containing 2% fetal calf serum, 0.3% bovine pituitary extract (Clonetics Corp.), 10 nanograms/ml TPA, 2 mM $CaCl_2$, 5 micrograms/ml insulin and 0.1 mM IBMX (Sigma).

(b) Chemicals

The beta-carotene was isolated from the alga *Dunaliella salina* and represented 85–90% of the total carotenoids, with half of the balance consisting of oxycarotenoids (lutein and zeaxanthin) and the remaining half of alpha-carotene. Gamma-carotene is normally undetectable as characterised by high pressure liquid chromatography. The soya bean oil was isolated from soya beans. A crystalline suspension of beta-carotene and soya bean oil was created: This resultant phase was then emulsified into the composition described. It was then sterilised by heat or filtration. Prior to testing on the cell lines each vial of the composition was sub-aliquoted into cryogenic vials (Costar) with a fresh vial used for each experiment. Throughout all procedures, beta0carotene was protected from direct light.

The details of the emulsified beta-carotene composition are as follows:

|  |  | % by weight |
|---|---|---|
| (i) and | Beta-carotene | 2.4% |
| (ii) | SOY being: |  |
|  | Soya bean oil | 6.8% |
|  | Glyceryl mono-oleate | 7.2% |
|  | Glycerol | 66.7% |
|  | Water | 16.9% |

This composition can be prepared by the following method. A crystalline suspension of beta-carotene in soya bean oil is heated and glyceryl mono-oleate is added. This oil phase is dispersed in the glycerol-water phase by high shear mixing followed by homogenization at 60–70° C. Typically, a homogenization pressure of 8,000 to 10,000 PSI is used, however, this pressure will vary according to the machine that is used. The resulting product is then sterilized by heat processing. Typically, heat processing is effected by autoclaving at 121° C. for 15 minutes in a pack for dispensing (3 ml glass vial). Optionally, 0.3% of the anti-oxidant tocopherols is added to overcome any toxicity that may develop over a period of time.

(c) Experimental Conditions

Ultra-violet ("UV") radiation can cause severe damage to cells, including genetic mutations, the promotion of cancer, and other adverse conditions. The potentially harmful effects for UV radiation for humans are mainly due to the UVB spectrum (ie, radiation having a wavelength of between 290 and 320 nanometers) (See: Gilchrest B A, Soler N A Staff J S and Mihm M C Jr: "The human sunburn reaction: histologic and biochemical studies" J, Am. Acad Dermatol. 5: 411–422 (1981)). Another form of UV radiation is called "UVC". UVC radiation in sunlight typically has a wavelength of the order of 254 nanometers. It is not as biologically relevant as UVB radiation however, because th UVC radiation in sunlight is strongly absorbed by the earth's ozone layer. accordingly, in the present study, we investigated the effects of UVB irradiation by melanocytes, and the changes to those effects by treating those cells with carotenoids. UVC wavelengths were blocked out of the experiments as the cells were incubated in plastic vessels. UVB irradiation of the melanocytes was performed with a Stratalinker Crosslinker (Stratagene) equipped with five UVP bulbs which exhibit an emission maximum centred at 302 nm as measured by a UVX-31 radiometer (UVP Inc.). Wavelengths shorter than 280 nm wee cut off by keeping lids on tissue culture dishes. FIG. 5 shows the spectrum distribution for the Stratalinker's UVP bulbs.

(d) RNA Analysis

Total RNA was isolated by detergent lysis followed by phenol-chloroform extraction and ethanol precipitation. 15 micrograms of RNA was size-fractionated on denaturing formaldehyde/agarose gels and transferred to nylon filters by capillary blotting. Blots were exposed to $^{32}$P-labelled cDNA probes and hybridized at 42° C. for 24 hours in 50% formamide, 2X SSC, 5X Denhardis, 0.1% SDS, 10% dextran sulfate and 100 micrograms/ml salmon sperm DNA. After hybridization, filters were washed to a stringency of 0.5–0.1X SSC at 60° C. and autoradiographed at −80° C. for three to ten days using Fuji film. Autoradiographs are quantitated by densitometry using the GS-365 software (Hoefer Scientific).

(e) Gene Probes

The c-jun probe was a 1.2 kb Sal 1/Hpa I fragment from the plasmid pHJ (Bohmann, 1987). The c-fos probe was a 1.8 kb Xbo 1/Eco R I fragment from the plasmid BK 28 (Verma, 1988). The 185 probe was isolated by an EcoRI digest and isolation of the 5.6 kb fragment from the plasmid pB (Gonzalez, 1988).

(f) Cell counting and DNA Synthesis Measurements

Cells were harvested with 0.25% trypsin and counted on a Coulter Counter (Coulter Instruments). Viability was determined by trypan blue exclusion. DNA synthesis was measured by labelling with (methyl-$^3$H)-thymidine (2.5 mCi/ml, 20 Ci/mmol, DuPont-New England Nuclear) added to the medium during the last 4 hours of incubation. Melanocytes were harvested using a Ph.D. cell harvester (Cambridge Research Inc.). the amount of radioactivity incorporated was determined by liquid scintillation counting (LS5000TD. Beckman Instruments).

(g) Nuclear Protein Extracts

Cells were grown to approximately 50–60% confluency and treated as described in the experimental protocol described in section (i) below. The cells were allowed to swell in hypotonic buffer (10 mM HEPES, pH 7.8, 0.1 mM EDTA, 10 mM KCC, 1 mM DTT. PMSF for 15 minutes on ice). Cytosolic protein fraction was obtained after the addition of Nonider P-40 to a final concentration of 0.5% and separation from the nuclei by centrifugation (500×g. for 5 minutes). Nuclear proteins were extracted from the remaining pellet by dialysis with hypertonic buffer (20 $\mu$M HEPES, pH 7.9, 350 mM NaCl, 1 Mm DTT, 1 mM PMSF) for 2 hours at 10° C. Isolated nuclear protein was frozen and stored at –80° C. Quantitation was calculated from optical density readings of 230, 260 and 320 wavelengths.

(h) Gel Mobility Shift Assays

Five microgram samples of each extract were incubated with 10,000 cpm of a $^{32}$p-labelled consensus oligonucleotide of NF Kappa B. Following a 1 hour incubation, samples were electrophoresed in a low ionic strength polyacrylamide gel. Quantitation of protein; DNA complexes was accomplished by densitometry.

Experimental Protocol

The following experimental timetable was adopted:

| | | UVB Irradiation | | | Assay Times | | |
|---|---|---|---|---|---|---|---|
| -48 | -24 | 0 | 0.0 5 | 1 | 2 | 4 | 24 |
| Melanocytes Plated | Beta Carotene 1 microgram/ml | Beta-carotene Removed, Irradiated, Media Witout Beta-carotene Added | | | Post Irradiation | | |

Normal human melanocytes were seeded into the appropriate vessel (6 well plate, 96 well plate, 75 cm or 175 cm flask) and allowed to grow to 50–60% confluency. In a "treated" group, fresh media and 1.0 microgram/ml of beta-carotene were then added and the cells were incubated for 24 hours with the beta-carotene After incubation, the cells were washed twice with PBS and exposed to 500 mJ/cm$^2$ of UV-B. Fresh media (without beta-carotene) was added following irradiation and cells were incubated for 1, 2, 4 and 24 additional hours. The 0.05 hour time indicates cells were harvested within 3 minutes following UV-B exposure. A "control" group received precisely the same treatment as the "treated" group, with the exception of being treated with beta-carotene.

Discussion of Results

FIG. 1 shows that while the DNA synthesis was largely inhibited at the highest beta-carotene dose, the lower doses had little or no effect. In this regard the 1.0 microgram/ml was chosen as the pre treatment dose for the UV experiments as it offered the highest beta-carotene concentration achievable with minimal effect on DNA synthesis. Beta-carotene was incubated with the melanocytes for 24 hours. Each data point is the mean of 6 wells +/–% std. error as compared to control.

FIG. 2 shows that immediately following 500 mJ/cm$^2$ of UV-B (0.05 hr), cell viability increased almost 20% with beta-carotene present as compared to UV-B alone. This effect remained for the duration of the time course. Each data point is the mean of 3 wells +/–% std. error as compared to controls.

FIG. 3 shows the largest induction of c-jun by UVB occurred 24 hours following a 500 mJ/cm$^2$ exposure (36.2 fold over basal level). Maximal induction of c-fos occurred 2 hours following irradiation with expression level 57 fold above basal. The induction of c-fos by UVB was essentially blocked by beta-carotene. C-jun expression was increased 11.1 fold by beta-carotene four hours following irradiation while at 24 hours the induction by UVB was completely blocked. Basal expression level of these genes without beta-carotene or UVB has been subtracted from all RNA levels shown. Blots were corrected for loading by 18S.

FIG. 4 shows that tritiated thymidine incorporation was increased 24 hours after irradiation in melanocytes treated with beta-carotene.

Without wishing to be limited to any specific theory, it appears that the mixture illustrated is a superfine emulsion.

Referring now to FIG. 6, the histograms shown in that figure are representative of four independent Northerns. On the left, are shown the results following 100 mJ/cm$^2$ UVB and on the right, the results following 500 ml are shown. As shown in the histograms in FIG. 6, c-fos and c-jun RNA levels increased rapidly, with the highest expression level reached one hour after irradiation. This induction was transient, however, as expression returned to basal levels×4 hours after irradiation. C-jun was at almost double the expression level at 1 hour following 500 mJ/cm$^2$, when compared with 100 mJ/cm$^2$ irradiation. C-fos expression was also higher subsequent to irradiation with 500 mJ/cm$^2$. Beta carotene did not alter the UVB-induced C-fos expression and had only a slight effect on the C-jun.

Referring now to FIG. 7, we then isolated nuclear protein from the melanocytes and looked at the DNA binding activities, subsequent to irradiation. The activity for the transcription factor NF kappa B was essentially unaffected over this time course. Nuclear factor Kappa B (NF kappa B) activation in the cytoplasm is known to be due to the dissociation of an inactive NF Kappa B-inhibitor of nuclear factor Kappa B complex. (See Simon, M M dt al: "UVB light induces Nuclear Factor Kappa B (NF Kappa B) activity independently from chromosomal DNA damage in cell-free cytosolic extracts": The Journal of Investigative Dermatology: 102 (No 4), 422 (April 1994)). However beta-carotene slightly decreased NF kappa B binding activity. although the dose of 100 mJ/cm$^2$ did not induce binding activity above basal level, beta-carotene did modify NF Kappa B activity.

FIG. 8 shows the results of DNA binding activity of normal Caucasian melanocytes following irradiation with 500 mJ/cm$^2$ UVB. A representative autoradiograph of NF Kappa B activity is shown to the left and a histogram of this to the right. The lowest activity level is seen 24 hours following irradiation.

in FIG. 7 beta-carotene was shown to have had a moderate effect on NF Kappa B at 100 mJ/cm$^2$, while at the higher dose of 500 mJ/cm$^2$, beta-carotene inhibited NF Kappa B activity by more than 50% in the first hour following irradiation. These data demonstrate that at the higher UVB dose, NF kappa B binding activity is down regulated.

FIG. 9 shows th results from Northern analysis of normal neo-natal Caucasian melanocytes cultured in TPA, as well as IBMX. We then looked at the effect of these media conditions on C-jun induction, subsequent to irradiation with 100 mJ/cm$^2$ of UVB. The melanocytes were treated with and without TPA and IBMX for 24 hours, then irradiated and incubated for an additional hour with and without the relevant factor. Compared to irradiated melanocytes in complete medium (ie medium which included both TPA and IBMX), C-jun induction decreased approximately 50%. In addition, the irradiated melanocytes lacking TPA and IBMX simultaneously reduced C-jun expression to the levels seen in all of the non-irradiated conditions. RNA levels were unaffected by the absence of TPA, IBMX or their combination in melanocytes not exposed to in UVB. At this low dose of 100 mJ/cm$^2$, it seems that melanocytes require both TPA and IBMX for complete induction of C-jun.

Conclusions

The scientific literature shows that a number of transcription factors are likely to be involved in response to DNA damage by ultraviolet radiation. These include the C-fos and C-jun genes, as well as the NF Kappa B complex, and the AP-1 complex. A schematic overview of the somewhat complex putative mechanisms involved in mediating the response to ultraviolet radiation damage to the DNA of normal melanocytes is depicted in FIG. 10. We conducted a series of experiments on cultured normal melanocytes (examined by Northern analysis for their expression of c-fos and c-jun, following exposure to ultraviolet-B (UVB) RADIATION). The data obtained from experiments which investigated the effect on c-fos and c-jun genes have presented somewhat conflicted outcomes. The discrepancies observed may be due to a number of influencing factors, such as the possibility that the ultraviolet radiation doses used are not appropriate for studying the effects of such irradiation in the c-fos and c-jun genes in epithelial cells, or the effects of carotenoids on the response evoked. Accordingly, it may be necessary to study the effects of irradiation and carotenoid treatments on these genes, under different experimental conditions. In addition, the possibility remains that other members of the jun and fos family of genes (eg, jun-B, jun-D, fos-B, fra I, fra II) could play a more significant role in the response to ultraviolet irradiation on normal epithelial cells, and the effect of beta-carotene on that response. These unresolved questions will required further investigation.

On the other hand, we have recently been able to conduct experiments which investigated the more recently discovered properties of the NF Kappa B complex, and the results of UV-damage response mediated by that complex. While we do not express here any definitive and binding theory to account for these observations, it appears that the NF Kappa B complex, is a more attenuated, and therefore more sensitive indicator of nucleic acid damage caused by ultraviolet irradiation to normal human melanocytes. Pre-treatment of such melanocytes with beta-carotene showed a statistically significant protective effect, particularly after one hour following UVB irradiation, at 500 mJ/cm$^2$. The protective effect was statistically significant at a p value of less than 0.05 (using the Student's t-test), Accordingly, it appears that the NF kappa B complex is the most appropriate model currently known for studying the conversion of melanocytes to melanomas, and the suppression of that process by beta-carotene.

The claims defining the invention are as follows:

1. A method of inhibiting carcinogen-mediated conversion of melanocyte cells to melanomas, comprising the step of administering to the cells an anti-tumorigenic composition comprising:

0.1 to 10% by weight of a water insoluble carotenoid; and 90 to 99.9% by weight of a non-toxic carrier medium including a suspending agent selected from the group consisting of fatty acids, triglyceride lipids, non-saponifiable lipids, and combinations thereof;

an emulsifier selected from the group consisting of a Tween polysorbate glycerol fatty acid esters and acetylated esters of fatty acids; and a water soluble dispersing agent which is a sugar or a polyol.

2. A method according to claim 1, wherein the conversion of melanocyte cells to melanomas is inhibited by modulating the activity of a DNA transcription factor.

3. A method according to claim 2, wherein the activity of the transcription factor is modulated by inhibiting expression of DNA.

4. A method according to claim 2, wherein the transcription factor includes at least one factor selected from the group consisting of NF kappa B complex-, AP-1 complex, C-fos gene products and C-jun gene products.

5. A method according to claim 4, wherein binding activity of NF kappa B complex is decreased.

6. A method of protecting DNA against carcinogen-mediated damage thereby to inhibit conversion of melanocyte cells to melanoma, comprising the step of administering to the cells a composition comprising 0.1 to 10% by weight of a water insoluble carotenoid which includes $\mu$-carotene; and 90 to 99.9% by weight of a non-toxic carrier medium including a suspending agent selected from the group consisting of fatty acids, triglyceride lipids, non-saponifiable lipid preparations, soluble hydrocarbons and combinations thereof;

an emulsifier selected from the group consisting of a Tween polysorbate glycerol fatty acid esters and acetylated esters of fatty acids; and a water soluble dispersing agent which is a sugar or a polyol.

7. A method according to claim 1 or claim 6, wherein the composition further comprises a diluent selected from the group consisting of cell growth medium, buffer, normal intravenous preparation, serum and combinations thereof;

wherein the normal intravenous preparation is isotonic saline or 5% dextrose.

8. A method according to claim 7, wherein the composition administrated to the cells comprises 0.5 to 3.0 $\mu$g beta-carotene per ml of the composition.

9. A method according to claim 8, wherein the composition administered to the cells comprises 0.1 $\mu$g beta-carotene per ml of the composition.

10. A method according to claim 1 or claim 6 wherein the carcinogen is radiation.

11. A method according to claim 10 wherein the radiation is UV radiation.

12. A method according to claim 1 or claim 6 wherein the melanocyte cells are of mammalian origin.

13. A method according to claim 1 or claim 6 wherein the melanocyte cells are of human origin.

14. A method according to claim 1 or claim 6 wherein the water insoluble carotenoid comprises at least 85% beta carotene.

15. A method according to claim 14 wherein the water insoluble carotenoid comprises from 85% to 90% of beta-carotene.

16. A method according to claim 1 or claim 6, wherein the water insoluble carotenoid comprises from 10% to 15% of oxycarotenoids and alpha-carotene.

17. A method according to claim 1 or claim 6, wherein the triglyceride lipids are selected from the group consisting of plant fats and oils and animal fats and oils.

18. A method according to claim 1 or claim 6, wherein the emulsifier is glycerol mono-oleate.

19. A method according to claim 1 or claim 6, wherein the water soluble dispersing agent is selected from the group consisting of sorbitol and glycerol.

* * * * *